ns with
only a negligible
United States Patent [19] [11] 3,935,237
Davidsohn [45] Jan. 27, 1976

[54] METHOD OF SULFONATION OF AROMATIC HYDROCARBONS WITH MINIMIZED BY-PRODUCT FORMATION
[75] Inventor: Alfred Davidsohn, Locarno, Switzerland
[73] Assignee: Marni S.A., Luxemburg
[22] Filed: Mar. 6, 1974
[21] Appl. No.: 448,637

[30] Foreign Application Priority Data
Mar. 10, 1973 Italy................................ 12524/73

[52] U.S. Cl............................ 260/505 E; 260/505 S
[51] Int. Cl.² ....................................... C07C 143/24
[58] Field of Search..................... 260/505 E, 505 S

[56] References Cited
UNITED STATES PATENTS
1,970,556 8/1934 Carswell ............................ 260/505
3,198,849 8/1965 Ballestra ............................ 260/505

Primary Examiner—James O. Thomas, Jr.
Assistant Examiner—A. Siegel
Attorney, Agent, or Firm—Robert E. Burns; Emmanuel J. Lobato; Bruce L. Adams

[57] ABSTRACT
The invention provides a method, applicable on an industrial scale, suitable to permit the production of sulphonated aromatic compounds with only a negligible formation of undesirable compounds.

11 Claims, 1 Drawing Figure

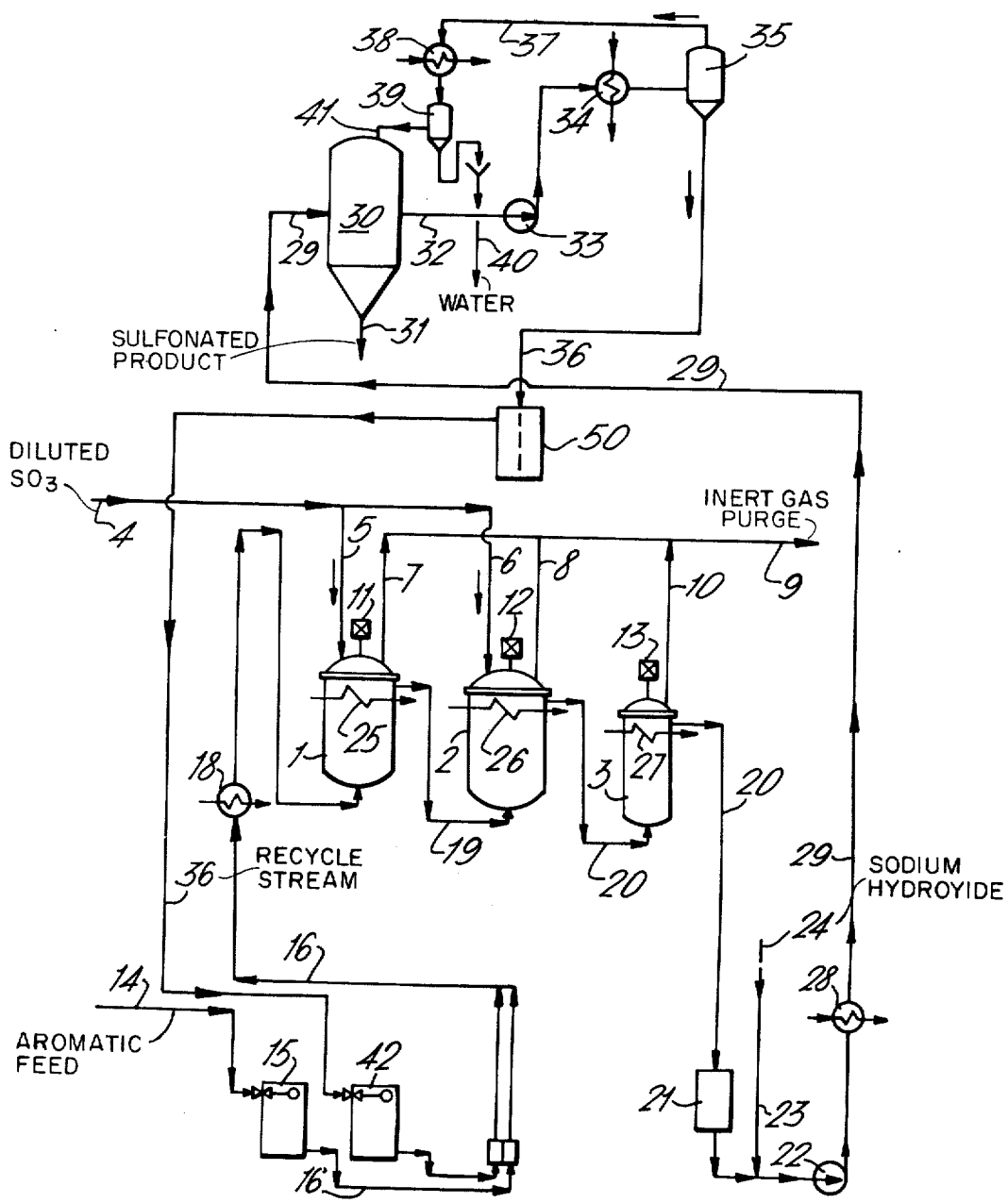

3,935,237

METHOD OF SULFONATION OF AROMATIC HYDROCARBONS WITH MINIMIZED BY-PRODUCT FORMATION

FIELD OF THE INVENTION

The present invention relates to an improved method for preventing undesired by-products from forming during the sulphonation or sulphation of organic aromatic compounds.

BACKGROUND OF THE INVENTION

It is known that during the sulphonation or sulphation of organic aromatic compounds, the final product desired tends to be highly contaminated by compounds coming from secondary reactions, said contaminating compounds are of course to be separated from the desired reaction product and that means reduction in yield and additional costs in processing. When on the other hand said contaminating compounds are left in the reaction product so as to save the separation costs, quality of said reaction product changes for the worse as said by-products modify the characteristics and purity thereof and particularly its smell, colour and solubility.

Such a condition occurs when oleum is used as the sulphonating agent, but increases considerably if, according to the latest technique, gaseous sulphur trioxide is used as sulphonating agent, the $SO_3$ is diluted in an inert carrier gas to reduce, at least partly, the reactivity thereof.

Particularly, when sulphonating aromatic compounds, a part of the amount of the fed $SO_3$ tends to bind itself, instead of to a single molecule of the aromatic compound to be sulphonated, to two molecules, thus forming a complex molecule of the compounds to be sulphonated, in general called a sulphone, said by-product when kept in the sulphonation mixture may itself undergo a further sulphonation process, giving sulphonated sulphones.

So, when sulphonating toluene, the desired final product consists of the toluene sulphonic acid (to be afterwards neutralized when required), while the undesired by-products are sulphones or sulphonated sulphones and other compounds.

Undesired compounds of the same nature are formed also when sulphonating benzene, xylene and similar aromatic hydrocarbon compounds.

Since, as said above, said by-products are undesirable, various attempts were made to limit their production during the sulphonation reaction. It is known for instance to this end to use small amounts of acetic acid which does not eliminate completely the production of those undesired compounds which at the end remain, though in small amounts, in the final product and must be separated therefrom. Further, there is a continuous loss of said acetic acid inhibiting agent, and said loss, though small in percent with respect to the treated product, is, at the end, considerable in absolute value when the process is performed in an industrial plant.

Up to date no method, applicable on an industrial scale to permit the production of sulphonated aromatic compounds with only a negligible formation of said undesired compounds, appears to be known.

OBJECTS OF THE INVENTION

A first object of the present invention is to overcome said disadvantage.

Particularly, it is further known that during the sulphonation of toluene the molecule of $SO_3$ may bind itself in one of the three possible ortho, meta and para positions. Conditions favouring the formation of a sulphonated compound in one or the other position are generally known. However, there are limits to obtain, in a practical, economically feasable manner, a sulphonated product only in para position or in the meta or ortho position respectively.

Another object of the invention is to obtain directly para-toluene-sulphonic acid, with yields up to 99% and more.

SUMMARY OF THE INVENTION

The improved method for preventing by-products from forming during the sulphonation of aromatic compounds, like benzene, toluene, xylene and the like, is to feed the product to be sulphonated into a reaction vessel or a successive series of vessels, to each of which is fed a fraction of the stoichiometrically required amount of the gaseous sulphonating reagent consisting of $SO_3$, diluted in an inert carrier gas. The sulphonic acid so obtained is afterwards, when required, subjected to neutralization, in a manner characterized by feeding the compound to be sulphonated to the various reaction steps in a large excess with respect to the amount of gaseous reagent fed in parallel to the various reaction stages; whereas the sulphonic acid formed in the reaction vessel as such or neutralized, is separated from the excess of the unsulphonated aromatic compound by the addition of the water or an aqueous solution used as solvent. The un-sulphonated aromatic compound, containing the reaction by-products dissolved therein, is recycled to the first reaction step so as to provide the required excess of the aromatic compound to be treated.

Said method is then further comprised in that the amount of gaseous reagent fed aggregately to the various reaction steps corresponds to about 5 – 50% of the stoichiometric quantity necessary to sulphonate completely the whole mass of the aromatic compound to be treated, said mass being fed to the first reaction step.

Said method also includes the aspect that when the desired sulphonic acid is a para-sulphonic acid, the reaction temperature is kept around 0°C.

Said method is further characterized in that the sulphonated sulphone formed as a by-product is used as the orienting agent to direct the sulphonation to the para position.

Said method also includes that when separating the water solution of the un-sulphonated aromatic compound mixture coming from the primary separation of the sulphonic acid as such or neutralized is distilled off, and the vapours still containing fractions of the un-sulphonated compounds are condensed, and then said fractions of the un-sulphonated aromatic compound which are separated from said water are recycled to the primary separation step of the sulphonic acid - water - solution from the un-sulphonated excess of aromatic compound.

BRIEF DESCRIPTION OF THE DRAWINGS

In order that the invention may be clearly understood, it will now be described, by way of example only, with reference to the accompanying drawing, wherein the single FIGURE shows a diagram of a plant suitable for the practice of the claimed method in the particular case when the aromatic compound to be sulphonated is represented by toluene.

DESCRIPTION OF A PREFERRED EMBODIMENT

With particular reference to the drawing, numerals 1 and 2 each denote a first and a second sulphonating device or vessel which are passed through in series by the product to be sulphonated and are fed in parallel by the gaseous reagent consisting of gaseous sulphur trioxide diluted in an inert carrier gas; numeral 3 denotes an ageing device or vessel wherein the sulphonation reaction between the compound to be sulphonated and the fractions of gaseous reagent still diluted therein is completed; 4 is the feeding conduit of the gaseous reagent $SO_3$ diluted in an inert carrier gas which, through branches 5 and 6, is fed into the reaction vessels 1 and 2, as for the vessels it is to be noted that it is possible to have a single one or more than two of them; numerals 7 and 8 denote two conduits for extracting the inert gases initially introduced or developed during the reaction, which are left free to leave the single reaction vessels 1 and 2 so as to be conveyed, through a common pipe 9, to a device for depurating and recovering the toluene carried over by partial pressure with the steam. To said pipe 9 is similarly conveyed the flow of exhaust gases coming from said ageing device 3, through a discharge pipe 10.

Said two reaction vessels 1 and 2 and device 3 are each provided with a stirring device driven by engines 11, 12 and 13. In this particular case, the aromatic compound to be treated consisting of toluene, is fed through a conduit 14 to a constant level tank 15 which is in position to intercept the feeding from 14 when its content reaches a given level. From here the compound to be treated is conveyed, through a conduit 16, to a pump B with variable delivery by an engine 17, the latter driving at the same time also a pump A with variable delivery whose function will be explained later on.

Downstream of pump B the compound to be treated is fed, still through 16, into the bottom of the first sulfonation reaction vessel after passing through a cooler 18; the liquid mixture, which by overflow leaves said reaction vessel 1 through a conduit 19 and has partly reacted, is conveyed towards the bottom of said second sulfonation stage reaction vessel 2; then said mixture leaves by overflow, through 20, said reaction vessel 2 and is fed to the bottom of aging device 3.

The liquid mixture leaves, by overflow, said device 3 and is conveyed, through said conduit 20, first to a proportionning device 21 and then to a mixing pump 22, the latter being at the same time fed with water only or an aqueous solution of caustic soda, through a conduit 23 coming from a plant for the production of said sodium hydroxide solution, denoted diagrammatically by 24.

It is now to be appreciated that the compound to be treated is fed in a large excess to reaction vessels 1 and 2, in the proportions stated herebelow, whereby said mixing pump 22 is reached, from conduit 20, by a liquid mixture consisting mainly of the compound to be treated and in a smaller proportion of the reaction product. Said two compounds are contaminated with various undesirable by-products, particularly with sulphones or sulphone-sulphonates corresponding to the compound to be treated, said sulphone, though being present in the range of some percent units, is however already contaminating the reaction product.

For said reaction vessels 1 and 2 and said device 3 a cooling heat exchanger plant, or generally a conditioning plant, may be further arranged, shown diagrammatically by 25, 26, 27.

The two phase liquid mixture consisting of the reaction product as such or neutralized, dissolved in water and the water imiscible the excess of the compound to be sulphonated, the undesirable by-products of the reaction, the water acting as a solvent for the reaction product, is fed from pump 22, after passing through the cooling means 28, to a separating means 30. From the bottom of said means 30 is extracted the sulfonated reaction product in aqueous solution through conduit 31. From the top is extracted, through conduit 32, the excess of the aromatic compound to be sulphonated containing the dissolved sulphones and fractions of water.

A pump 33 conveys said mixture first to a heater 34 and then to an evaporator 35 from the bottom of which the un-sulphonated product mixed with the undesired by-product dissolved therein comes out through a pipe 36.

The steam containing fractions of un-sulphonated compound, comes out of the top of an evaporator 35 through 37; said mixture, after being cooled in a cooler 38, is separated in a secondary separating device 39. From said device 39 and through 40, the water is discharged, while the un-sulphonated compound is conveyed back again to the main separating system 30 through a pipe 41.

Through said conduit 36 the mixture of un-sulphonated aromatic compound and reaction by-product, after stopping in a tank 50, is conveyed to a constant level tank 42 and from here, through said pump A, is mixed within said pipe 16 with the fresh aromatic compound to be treated coming from said tank 15.

As the reactivity of the gaseous reagent consisting of dilute $SO_3$ with the aromatic compounds of either toluene, benzene and xylene is very high, an expert in the art might not consider it correct to feed the compound to be treated in a large excess with respect to $SO_3$. Neither can the dilution of the sulphonation product into the product to be treated in excess be justified, according to the known art, by the need of lowering the reaction temperature, as the sulphonation reaction is highly exothermic; in fact, as was shown by previous patents, the separation of the sulphonation reaction in more stages permits keeping of the reaction temperature within a range which is not dangerous for the reaction product. It is further to be noted that, in contrast to what would appear logical, no provision is made in any method similar to the one described, for separating from the excess aromatic compound still unsulphonated, coming from 36, the undesired by-products of the reaction, mainly the sulphone and the sulphonated sulphones, which then go back to cycle through 16 into the reaction vessels 1 and 2.

As a matter of fact, it was surprisingly found that when in the liquid mixture formed by the compound to be sulphonated and the product of the sulphonation reaction is present, a given concentration of said sulphone accumlated, said concentration acts as a preventing agent against the successive formation of additional undesired compound.

At the same time and surprisingly as well, the sulphonated sulphone acts as an orienting agent for the $SO_3$ group to appear in the para position.

On the other hand, as said by-products are non-soluble in the reaction product after the water dilution or aqueous soda solution neutralization step, they are not present in the pure reaction product coming out of said main separator 30, but remain almost completely within said un-sulphonated aromatic compound which, through 36, 42 and A, recycled into the two reaction vessels.

The effect thus obtained is that, after starting the plant when same works normally, there is a substantially stoichiometric consumption of the aromatic compound to be sulphonated and the gaseous reagent consisting of $SO_3$, and on the other side the production of the sulphonated compound, as such or neutralized and completely free of by-products; therefore, for said by-products there is no problem for their disposal, as in a normal operation their hourly production is substantially nul and the amount of sulphone by product circulating within the plant system remains constant.

According to a preferred embodiment of the method according to the invention, same may be advantageously used for the production of sulphonated aromatic compounds sulfonated primarily in the para position, and whose percent of sulphonated compounds in the meta and orto positions may be reduced to some small percentage units.

According to said method, by sulphonating at the temperatures of $-10°C$ to $+10°C$ and using the sulphonated sulphone as orienting agent in the para position, it is possible to obtain a production of mixtures of isomers wherein the percent of para isomers reaches 99%.

Still by way of example the operative conditions for a plant suitable to produce 1000 kg/h of toluene sulphonic acid, are described herebelow.

The $SO_3$ diluted in said inert carrier gas is obtained from the combustion of molten sulphur and the successive passage of the $SO_2$ produced in a catalyst tower where it is transformed into $SO_3$. For the combustion of said molten sulphur, an excess of dry water is used so as to dilute said gaseous $SO_3$ to about 9% by volume.

In normal operative conditions 535 kg/h of toluene and about 200 kgs. of sulphur are used.

For the production of the sodium salt of the sulphonic toluene acid 240 kgs/h of NaOH at 100% are used and for the neutralization 1500 kgs/h of water suitable to dilute the caustic soda. When the neutralization is not required, only water is added. The amount of toluene fed continuously to said reaction vessel 1 is however largely in excess with respect to the amount of $SO_3$ reaching aggregately said reaction vessels 1 and 2. Said amount of $SO_3$ is about 30% of the quantity stoichiometrically necessary for the sulphonation of the toluene coming from 16. Therefore, if through conduit 14 is fed a quantity of toluene equal to 535 kgs/h, the hour delivery of the recycle conduit for the toluene is equal to 1250 kgs/h. The amount of di-toluene sulphone circulating within conduit 36 in the recycled toluene is 1 - 2% by weight. However, such a modest amount of reaction by-product is sufficient to work as a preventing agent inside said reaction vessels 1 and 2, and thus it prevents any further formation and accumulation of di-toluene sulphone.

The average composition of the product obtained in this case was the following (for 1000 kgs. of sulphonic toluene acid produced):

| | |
|---|---|
| para toluene sulphonic acid | 97.91% (99.5% on the mixture of isomers |
| orto and meta-toluene sulphonic acid | 0.49% max.(0.5 on isomers) |
| sulfuric acid | 1.5% max. |
| di-toluene sulphone | 0.1% max. |

It is to be understood that the invention is not limited to the examples shown. It is intended to cover all modifications and equivalents within the scope of the appended claims.

What I claim is:

1. An improved method for the sulfonation of aromatic hydrocarbon compounds by a gaseous reagent consisting of reactant $SO_3$ diluted in inert diluent gases which comprises the steps of:
    A. introducing the aromatic compound into a first of a plurality of reaction vessels;
    B. feeding less than the stiochiometrically-required amount of the gaseous reagent of $SO_3$, diluted in inert gases, into each of said reaction vessels to react with a portion of said aromatic compound to form a liquid mixture in said vessel of (a) unreacted excess aromatic compound, (b) the sulfonic acid product produced by the reaction of the aromatic compound with the $SO_3$; and (c) some by-products, said by-products being soluble in said unreacted excess aromatic compound;
    C. removing said mixture from said reaction vessels to a separation vessel;
    D. separating said sulfonation product (b), from said unreacted excess aromatic compound (a) containing said dissolved by-product (c);
    E. recovering said sulfonated product (b);
    F. recycling to said first reaction vessel the unreacted aromatic compound (a) containing dissolved therein said by-products (c), whereby said by-products (c) achieve an inhibiting concentration for said by-product formation in said aromatic compound within the reaction vessels.

2. The method according to claim 6 wherein an aqueous separating agent is added to said separation vessel in step C to form at least two immiscible liquid phases consisting of a heavier aqueous phase comprising an aqueous solution of the sulfonation reaction product (b) and a substantially waterimmiscible phase containing said unreacted excess of aromatic compound (a) having dissolved therein said by-products (c).

3. The method according to claim 2 wherein said aqueous separating agent is water.

4. The method according to claim 2 wherein said aqueous separating agent is an aqueous caustic soda solution and said acid product is recovered in the form of the sodium salt of the sulfonic acid.

5. The method according to claim 1 wherein said aromatic compound is selected from the group consisting of benzene toluene and xylene.

6. The method according to claim 1 wherein said aromatic compound is introduced into a first and successively into a plurality of vessels, each of which is fed with a fraction of said gaseous reagents.

7. The method according to claim 1 wherein the entire amount of gaseous reagent fed to all the vessels corresponds to about 5–50% of the amount of $SO_3$ stoichiometrically necessary for sulphonating the entire amount of said aromatic compound, said entire amount consisting of fresh compound and recycled compound, which entire amount is fed to said first vessel.

8. The method according to claim 1, wherein the sulphonic acid product is a para-oriented aralkyl-sulphonic acid and the reaction vessel temperature is maintained at about $-10°C$ to $+10°C$.

9. The method according to claim 8, wherein the recycled by-product is used as an orienting agent to direct the sulphonation of aralkyl aromatic compounds to the para position.

10. A method according to claim 2, wherein the separation of the aqueous solution containing said product from the excess aromatic compound mixture coming from the separation step is distilled and any vapors containing any volatilized fractions of the excess of unreacted aromatic compound are condensed, and then said fractions of the unreacted aromatic compound are decanted from the water and are recycled to said primary separation step to separate the aqueous solution of the product.

11. An improved method according to claim 4, wherein the separation of the caustic solution of the product from the excess aromatic compound mixture from the separation step is distilled and the vapors containing any volatilized fractions of the excess aromatic compound are condensed, and then said condensate fractions of the aromatic compound are decanted from the water and are recycled to the primary separation step to separate the caustic aqueous solution of the product.

* * * * *